US010428129B2

(12) United States Patent
Peng et al.

(10) Patent No.: US 10,428,129 B2
(45) Date of Patent: Oct. 1, 2019

(54) RECOMBINANT PROTEIN

(71) Applicant: UBI PHARMA INC, Hukou Township, Hsinchu County (TW)

(72) Inventors: Wen-Jiun Peng, Hukou Township, Hsinchu County (TW); Shu-Ping Yang, Hukou Township, Hsinchu County (TW); Hung-Chih Peng, Hukou Township, Hsinchu County (TW); Yu-Hung Chen, Hukou Township, Hsinchu County (TW)

(73) Assignee: UBI PHARMA INC., Hukou Township, Hsinchu County (TW)

( * ) Notice: Subject to any disclaimer, the term of this patent is extended or adjusted under 35 U.S.C. 154(b) by 0 days.

(21) Appl. No.: 14/653,838

(22) PCT Filed: Dec. 16, 2013

(86) PCT No.: PCT/CN2013/089544
§ 371 (c)(1),
(2) Date: Jun. 18, 2015

(87) PCT Pub. No.: WO2014/094579
PCT Pub. Date: Jun. 26, 2014

(65) Prior Publication Data
US 2016/0176940 A1     Jun. 23, 2016

(30) Foreign Application Priority Data
Dec. 18, 2012 (CN) .......................... 2012 1 0551666

(51) Int. Cl.
| C07K 14/505 | (2006.01) |
| C12N 15/62 | (2006.01) |
| C07K 14/52 | (2006.01) |
| C07K 14/59 | (2006.01) |
| C07K 14/575 | (2006.01) |
| A61K 38/00 | (2006.01) |

(52) U.S. Cl.
CPC .......... *C07K 14/505* (2013.01); *C07K 14/524* (2013.01); *C07K 14/575* (2013.01); *C07K 14/59* (2013.01); *A61K 38/00* (2013.01); *C07K 2319/00* (2013.01); *C07K 2319/31* (2013.01)

(58) Field of Classification Search
None
See application file for complete search history.

(56) References Cited

U.S. PATENT DOCUMENTS

| 5,272,071 | A | 12/1993 | Chappel |
| 5,547,933 | A | 8/1996 | Lin |
| 5,621,080 | A | 4/1997 | Lin |
| 5,641,670 | A | 6/1997 | Treco |
| 5,733,761 | A | 3/1998 | Treco |
| 5,981,214 | A | 11/1999 | Skoultchi |

| 7,217,689 | B1 | 5/2007 | Elliott | |
| 2002/0160944 | A1* | 10/2002 | Boime | .................. C07K 14/59 530/398 |
| 2003/0124115 | A1* | 7/2003 | Lee | ...................... C07K 14/505 424/94.64 |
| 2007/0190610 | A1* | 8/2007 | Fares | .................. C07K 14/505 435/69.1 |
| 2007/0184530 | A1 | 9/2007 | Fares | |
| 2009/0221037 | A1 | 9/2009 | Lee et al. | |
| 2009/0238789 | A1 | 9/2009 | Guyon | |

FOREIGN PATENT DOCUMENTS

| CN | 1421461 | 6/2003 |
| CN | 101337988 | 1/2009 |
| CN | 101678079 | 3/2010 |
| EP | 1319712 | 6/2003 |
| GB | 2382580 A * | 6/2003 |
| JP | H11-155584 | 6/1999 |
| JP | 2003-169671 | 6/2003 |
| JP | 2004-515246 | 5/2004 |
| JP | 2009-525052 | 7/2009 |
| JP | 2010-510794 | 4/2010 |
| JP | 2010-213699 | 9/2010 |
| TW | 1237056 | 8/2005 |
| WO | 1995/005465 | 2/1995 |
| WO | 2002/048194 | 6/2002 |
| WO | 2003/046013 | 6/2003 |
| WO | 2007/094985 | 8/2007 |
| WO | 2008/065372 | 6/2008 |
| WO | 2000/028066 | 5/2010 |

OTHER PUBLICATIONS

US 5,733,746 A, 03/1998, Treco (withdrawn)
Lee et al. The prolonged half-lives of new eythropoietin derivatives via peptide additon. Biochemical and Biophysical Research Communication vol. 339:380-385 (2006).*
Wells, J.A. Additivity of Mutational Effects in Proteins. Biochemistry 29:8509-8517 (1990).*
Ngo et al. Computational Complexity, Protein Structure Prediction and the Levinthal Paradox. The Protein Folding Problem and Tertiary Structure Prediction, pp. 433-440 and 492-495 (1994).*
Tokuriki et al., Stability effects of mutations and protein evolvability; Current Opinion in Structural Biology, 19:596-604 (2009).*
Egrie, J.C., et al.; "Pharmacokinetics of recombinant human erythropoietin"; Kidney Int 33(1):262 4 (1988).
GenBank Accession No. ACI13658, Version ACI13658.1, Jan. 27, 2009, retrieved from NCBI (online) on Mar. 10, 2014, (URL: http://www.ncbi.nlm.nih.gov).
Krantz, S.B., "Erythropoietin"; Blood. Feb. 1, 1991;77(3):419-34.
Lai, P.H, et al.; "Structural characterization of human erythropoietin"; J. Biol. Chem. 261(7):3116-3121 (1986).

(Continued)

*Primary Examiner* — Elizabeth C. Kemmerer
*Assistant Examiner* — Regina M DeBerry
(74) *Attorney, Agent, or Firm* — Locke Lord, LLP; Brandon T. Schurter

(57) ABSTRACT

A recombinant protein is provided. The recombinant protein of the invention comprises an erythropoietin and a highly glycosylated peptide, and has a longer half-life. Further, the recombinant protein of the invention may also comprise a carboxyl-terminal peptide of human chorionic gonadotropin and a carboxyl-terminal peptide of thrombopoietin.

14 Claims, 5 Drawing Sheets

Specification includes a Sequence Listing.

(56) References Cited

OTHER PUBLICATIONS

Lee-Huang, S., "Cloning and expression of human erythropoietin cDNA in *Escherichia coli*"; PNAS 1984 81 (9) 2708-2712.
Sasaki, H., et al.; "Carbohydrate structure of erythropoietin expressed in Chinese hamster ovary cells by a human erythropoietin cDNA"; J Biol Chem. Sep. 5, 1987;262(25):12059-76.
English Translation of the International Search Report issued in corresponding International Application No. PCT/CN2013/089544, dated Mar. 20, 2014.
English Translation of the Written Opinion of the International Searching Authority issued in corresponding International Application No. PCT/CN2013/089544, dated Mar. 20, 2014.
English Translation of the International Preliminary Report on Patentability issued in corresponding International Application No. PCT/CN2013/089544, dated Jun. 23, 2015.
Search Report issued in corresponding Chinese Patent Application No. CN201210551666.7 (now CN Patent Publication No. CN105102483B), dated Jun. 23, 2015.
Translated Search Report issued in corresponding Japanese Patent Application No. JP2015-548170 (now JP Patent No. JP6083913B2), dated Apr. 1, 2016.
Conley, A.J., et al., "Plant recombinant erythropoietin attenuates inflammatory kidney cell injury", Plant Biotechnol. J., 7(2):183-199 (2009) (Epub 2008).
Molecular Cell Biology Dictionary, p. 143, 2nd edition, Tokyo Chemical Doujin, ISBN: 978-4-8079-0687-1 (2008) (In Japanese only, cited as an "A" document in JP Search Report to describe the general state of the art).
Biochemistry Dictionary, 3rd edition, p. 21, Inoue Shinzo, Tokyo Chemical Doujin, ISBN: 4-8079-0480-9 (1998) (In Japanese only, cited as an "A" document in JP Search Report to describe the general state of the art).
Cold Spring Harbor, Sugar Chain Biology, Chapter 7, N-glycan, Maruzen Company, Ltd, ISBN: 4-621-07292-7 (2003) (In Japanese only, cited as an "A" document in JP Search Report to describe the general state of the art).

* cited by examiner

SEQUENCE LISTING

```
<160> NUMBER OF SEQ ID NOS: 17

<210> SEQ ID NO 1
<211> LENGTH: 20
<212> TYPE: PRT
<213> ORGANISM: Artificial sequence
<220> FEATURE:
<223> OTHER INFORMATION: Synthetic highly glycosylated peptide

<400> SEQUENCE: 1

Glu Ala Glu Asn Ile Thr Thr Gly Gly Asn Glu Thr Gly Ser Leu Asn
1               5                   10                  15

Glu Asn Ile Thr
            20

<210> SEQ ID NO 2
<211> LENGTH: 17
<212> TYPE: PRT
<213> ORGANISM: Artificial sequence
<220> FEATURE:
<223> OTHER INFORMATION: Synthetic highly glycosylated peptide

<400> SEQUENCE: 2

Val Pro Asp Leu Leu Val Asn Ser Ser Gln Val Asn Glu Thr Leu Gln
1               5                   10                  15

Leu

<210> SEQ ID NO 3
<211> LENGTH: 28
<212> TYPE: PRT
<213> ORGANISM: Homo sapiens

<400> SEQUENCE: 3

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 4
<211> LENGTH: 17
<212> TYPE: PRT
<213> ORGANISM: Homo sapiens

<400> SEQUENCE: 4

Pro Leu Leu Asn Thr Ser Tyr Thr His Ser Gln Asn Leu Ser Gln Glu
1               5                   10                  15

Gly

<210> SEQ ID NO 5
<211> LENGTH: 275
<212> TYPE: PRT
<213> ORGANISM: Artificial Sequence
<220> FEATURE:
<223> OTHER INFORMATION: Recombinant EPO-NNCT

<400> SEQUENCE: 5

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
            35                  40                  45
```

-continued

```
Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg Glu Ala Glu Asn Ile Thr Thr Gly Asn Glu Thr Gly Ser Leu
            195                 200                 205

Asn Glu Asn Ile Thr Val Pro Asp Leu Leu Val Asn Ser Ser Gln Val
210                 215                 220

Asn Glu Thr Leu Gln Leu Ser Ser Ser Lys Ala Pro Pro Ser
225                 230                 235                 240

Leu Pro Ser Pro Ser Arg Leu Pro Gly Pro Ser Asp Thr Pro Ile Leu
                245                 250                 255

Pro Gln Pro Leu Leu Asn Thr Ser Tyr Thr His Ser Gln Asn Leu Ser
                260                 265                 270

Gln Glu Gly
275

<210> SEQ ID NO 6
<211> LENGTH: 275
<212> TYPE: PRT
<213> ORGANISM: Artificial Sequence
<220> FEATURE:
<223> OTHER INFORMATION: Recombinant NNCT-EPO

<400> SEQUENCE: 6

Glu Ala Glu Asn Ile Thr Thr Gly Gly Asn Glu Thr Gly Ser Leu Asn
 1               5                  10                  15

Glu Asn Ile Thr Val Pro Asp Leu Leu Val Asn Ser Ser Gln Val Asn
                 20                  25                  30

Glu Thr Leu Gln Leu Ser Ser Ser Lys Ala Pro Pro Ser Leu
             35                  40                  45

Pro Ser Pro Ser Arg Leu Pro Gly Pro Ser Asp Thr Pro Ile Leu Pro
 50                  55                  60

Gln Pro Leu Leu Asn Thr Ser Tyr Thr His Ser Gln Asn Leu Ser Gln
 65                  70                  75                  80

Glu Gly Met Gly Val His Glu Cys Pro Ala Trp Leu Trp Leu Leu
                 85                  90                  95

Ser Leu Leu Ser Leu Pro Leu Gly Leu Pro Val Leu Gly Ala Pro Pro
            100                 105                 110

Arg Leu Ile Cys Asp Ser Arg Val Leu Glu Arg Tyr Leu Leu Glu Ala
            115                 120                 125
```

```
Lys Glu Ala Glu Asn Ile Thr Thr Gly Cys Ala Glu His Cys Ser Leu
130                 135                 140

Asn Glu Asn Ile Thr Val Pro Asp Thr Lys Val Asn Phe Tyr Ala Trp
145                 150                 155                 160

Lys Arg Met Glu Val Gly Gln Gln Ala Val Glu Val Trp Gln Gly Leu
            165                 170                 175

Ala Leu Leu Ser Glu Ala Val Leu Arg Gly Gln Ala Leu Leu Val Asn
            180                 185                 190

Ser Ser Gln Pro Trp Glu Pro Leu Gln Leu His Val Asp Lys Ala Val
            195                 200                 205

Ser Gly Leu Arg Ser Leu Thr Thr Leu Leu Arg Ala Leu Gly Ala Gln
210                 215                 220

Lys Glu Ala Ile Ser Pro Pro Asp Ala Ala Ser Ala Ala Pro Leu Arg
225                 230                 235                 240

Thr Ile Thr Ala Asp Thr Phe Arg Lys Leu Phe Arg Val Tyr Ser Asn
                245                 250                 255

Phe Leu Arg Gly Lys Leu Lys Leu Tyr Thr Gly Glu Ala Cys Arg Thr
            260                 265                 270

Gly Asp Arg
        275

<210> SEQ ID NO 7
<211> LENGTH: 230
<212> TYPE: PRT
<213> ORGANISM: Artificial Sequence
<220> FEATURE:
<223> OTHER INFORMATION: Recombinant EPO-N1N2

<400> SEQUENCE: 7

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg Glu Ala Glu Asn Ile Thr Thr Gly Gly Asn Glu Thr Gly Ser Leu
        195                 200                 205
```

Asn Glu Asn Ile Thr Val Pro Asp Leu Leu Val Asn Ser Ser Gln Val
            210                 215                 220

Asn Glu Thr Leu Gln Leu
225                 230

<210> SEQ ID NO 8
<211> LENGTH: 230
<212> TYPE: PRT
<213> ORGANISM: Artificial Sequence
<220> FEATURE:
<223> OTHER INFORMATION: Recombinant N1N2-EPO

<400> SEQUENCE: 8

Glu Ala Glu Asn Ile Thr Thr Gly Gly Asn Glu Thr Gly Ser Leu Asn
1               5                   10                  15

Glu Asn Ile Thr Val Pro Asp Leu Leu Val Asn Ser Ser Gln Val Asn
            20                  25                  30

Glu Thr Leu Gln Leu Met Gly Val His Glu Cys Pro Ala Trp Leu Trp
        35                  40                  45

Leu Leu Leu Ser Leu Leu Ser Leu Pro Leu Gly Leu Pro Val Leu Gly
    50                  55                  60

Ala Pro P

```
Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg Glu Ala Glu Asn Ile Thr Thr Gly Gly Asn Glu Thr Gly Ser Leu
        195                 200                 205

Asn Glu Asn Ile Thr
210

<210> SEQ ID NO 10
<211> LENGTH: 210
<212> TYPE: PRT
<213> ORGANISM: Artificial Sequence
<220> FEATURE:
<223> OTHER INFORMATION: Recombinant EPO-N2

<400> SEQUENCE: 10

Met Gly Val His Glu Cys Pro Ala Trp Leu Trp Leu Leu Ser Leu
1                5                  10                  15

Leu Ser Leu Pro Leu Gly Leu Pro Val Leu Gly Ala Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190
```

-continued

Arg Val Pro Asp Leu Leu Val Asn Ser Ser Gln Val Asn Glu Thr Leu
        195                 200                 205

Gln Leu
    210

<210> SEQ ID NO 11
<211> LENGTH: 76
<212> TYPE: DNA
<213> ORGANISM: Artificial Sequence
<220> FEATURE:
<223> OTHER INFORMATION: LSP-N-S1 primer

<400> SEQUENCE: 11
cctagggcca ccatgggggt gcacgaatgt cctgcctggc tgtggcttct cctgtccctg    60
ctgtcgctcc ctctgg                                                    76

<210> SEQ ID NO 12
<211> LENGTH: 72
<212> TYPE: DNA
<213> ORGANISM: Artificial Sequence
<220> FEATURE:
<223> OTHER INFORMATION: LSP-N-S2 primer

<400> SEQUENCE: 12
ctgtccctgc tgtcgctccc tctgggcctc ccagtcctgg gcgaggccga gaatatcacg    60
acgggcggta ac                                                        72

<210> SEQ ID NO 13
<211> LENGTH: 69
<212> TYPE: DNA
<213> ORGANISM: Artificial Sequence
<220> FEATURE:
<223> OTHER INFORMATION: ENNCT1-A primer

<400> SEQUENCE: 13
ctcggctgtc acagatgagg cgtggtgggg ccccttcctg agacagattc tgggagtggg    60
tgtaggatg                                                            69

<210> SEQ ID NO 14
<211> LENGTH: 36
<212> TYPE: DNA
<213> ORGANISM: Artificial Sequence
<220> FEATURE:
<223> OTHER INFORMATION: E-S primer

<400> SEQUENCE: 14
cctagggcca ccatgggggt gcacgaatgt cctgcc                              36

<210> SEQ ID NO 15
<211> LENGTH: 40
<212> TYPE: DNA
<213> ORGANISM: Artificial Sequence
<220> FEATURE:
<223> OTHER INFORMATION: ENNCT2-A primer

<400> SEQUENCE: 15
gtatacctac agctgcagag tctcgttcac ctgggaagag                          40

<210> SEQ ID NO 16
<211> LENGTH: 30
<212> TYPE: DNA
<213> ORGANISM: Artificial Sequence
<220> FEATURE:
<223> OTHER INFORMATION: ENNCT4-A primer

```
<400> SEQUENCE: 16
gtatacctag tctgggacag tgatattctc                              30

<210> SEQ ID NO 17
<211> LENGTH: 77
<212> TYPE: DNA
<213> ORGANISM: Artificial Sequence
<220> FEATURE:
<223> OTHER INFORMATION: ENNCT5-A primer

<400> SEQUENCE: 17
gtatacctac agctgcagag tctcgttcac ctgggaagag ttgaccaaca gtctgtcccc    60
tgtcctgcag gcctccc                                            77
```

RECOMBINANT PROTEIN

This application is a national phase entry under 35 U.S.C. § 371 of International Application Number PCT/CN2013/089544, filed Dec. 16, 2013, entitled "RECOMBINANT PROTEIN", which claims the benefit of Chinese Patent Application Number CN 201210551666.7, filed Dec. 18, 2012, all of which are hereby incorporated by reference in their entireties.

FIELD OF THE INVENTION

The present invention relates to a recombinant protein, and in particular relates to a highly glycosylated erythropoietin (EPO) with a longer half-life.

BACKGROUND OF THE INVENTION

Erythropoietin (EPO) is a glycoprotein hormone, or a cytokine for red blood cell precursors in the bone marrow. In humans, erythropoietin is involved in the production of red blood cells, and hormone regulation. Simultaneously, erythropoietin also has other biological functions. For example, erythropoietin is involved in the process of wound healing when nerve damage is present.

Erythropoiesis is the production of red blood cells, which occurs to offset cell destruction. Erythropoiesis is a controlled physiological mechanism that enables sufficient red blood cells to be available for proper tissue oxygenation. Naturally occurring human erythropoietin (hEPO) is produced in the kidney and is the humoral plasma factor which stimulates red blood cell production (Carnot, P and Deflandre, C (1906) C. R. Acad. Sci. 143: 432; Erslev, A J (1953 Blood 8: 349; Reissmann, K R (1950) Blood 5: 372; Jacobson, L O, Goldwasser, E, Freid, W and Plzak, L F (1957) Nature 179: 6331-4). EPO stimulates the division and differentiation of committed erythroid progenitors in the bone marrow and exerts its biological activity by binding to receptors on erythroid precursors (Krantz, B S (1991) Blood 77: 419).

Erythropoietin has been manufactured biosynthetically using recombinant DNA technology (Egrie, J C, Strickland, T W, Lane, J et al. (1986) Immunobiol. 72: 213-224) and is the product of a cloned human EPO gene inserted into and expressed in the ovarian tissue cells of the Chinese hamster (CHO cells). The molecular weight of the polypeptide chain of EPO without the sugar moieties is 18,236 Da. In the intact EPO molecule, approximately 40% of the molecular weight is accounted for by the carbohydrate groups that glycosylate the protein at glycosylation sites on the protein (Sasaki, H, Bothner, B, Dell, A and Fukuda, M (1987) J. Biol. Chem. 262: 12059).

Because human erythropoietin is essential in red blood cell formation, the hormone is useful in the treatment of blood disorders characterized by low or defective red blood cell production. Clinically, EPO is used in the treatment of anemia in chronic renal failure patients (CRF) (Eschbach, J W, Egri, J C, Downing, M R et al. (1987) NEJM 316: 73-78; Eschbach, J W, Abdulhadi, M H, Browne, J K et al. (1989) Ann. Intern. Med. 111: 992; Egrie, J C, Eschbach, J W, McGuire, T, Adamson, J W (1988) Kidney Intl. 33: 262; Lim, V S, Degowin, R L, Zavala, D et al. (1989) Ann. Intern. Med. 110: 108-114) and in AIDS and cancer patients undergoing chemotherapy (Danna, R P, Rudnick, S A, Abels, R I In: M B, Garnick, ed. Erythropoietin in Clinical Applications—An International Perspective. New York, N.Y.: Marcel Dekker; 1990: p. 301-324). However, the bioavailability of EPO protein treatment is limited by its short plasma half-life and protease degradation, making it hard to attain good clinical efficacy.

SUMMARY OF THE INVENTION

The invention provides a highly glycosylated erythropoietin (EPO) with a long half-life.

In order to achieve the goal, the invention provides a recombinant protein comprising an erythropoietin and a highly glycosylated peptide.

The invention further provides a nucleotide encoding the recombinant protein.

The invention also provides a cell which is transfected with the nucleotide to express the recombinant protein.

The invention further provides a composition, comprising the recombinant protein and a pharmaceutically acceptable carrier or adjuvant.

In order to achieve the purpose stated above, as well as other purposes, the characteristics and advantages of the present invention can be more apparent and understandable, and preferred embodiments are exemplified in the following with accompanying drawings to aid in detailed interpretation.

DETAILED DESCRIPTION OF THE INVENTION

The present invention provides a recombinant erythropoietin with a long half-life and a manufacture method thereof.

In one embodiment, the present invention provides a recombinant protein comprising an erythropoietin and a highly glycosylated peptide.

As used herein, the phrase "erythropoietin (EPO)" includes EPO of every origin, especially human or animal EPO. The term used herein encompasses not only the naturally occurring, that is wild-type forms of EPO, but also its derivatives, analogs, modifications, mutants or others, as long as they show the biological effects of wild-type erythropoietin.

Any protein having the activity of EPO, such as muteins or otherwise modified protein, is also encompassed. Recombinant EPO may be prepared via expression in CHO, BHK, COS, HeLa or PER.C6 cell lines or other appropriate cell lines, by recombinant DNA technology and the related content can be referred to U.S. Pat. Nos. 5,733,761, 5,641,670, 5,733,746, 5,994,122, 5,733,761, 5,641,670, 5,981,214 and 5,272,071. Its preparation and therapeutic application can be referred to U.S. Pat. Nos. 5,547,933 and 5,621,080, Huang, S. L., Proc. Natl. Acad. Sci. USA (1984) 2708-2712, as well as Lai, P. H. et al., J. Biol. Chem. 261 (1986) 3116-3121, an Sasaki, H. et al., J. Biol. Chem. 262 (1987) 12059-12076. The preferred species for EPO is human.

As used herein, the phrase "highly glycosylated peptide" refers to a polypeptide having about 10 to 30 amino acid residues with at least one glycoside. The highly glycosylated peptide of the present invention includes one or more N- or O-linked glycosylation site(s) for producing one or more glycan(s). For example, a sequence of SEQ ID NO: 1 and/or 2, or a sequence having at least 60%, 65%, 70%, and 80% sequence identity to SEQ ID NO: 1 or 2, preferably, 90%, 95%, or 99% sequence identity.

Figure 1:
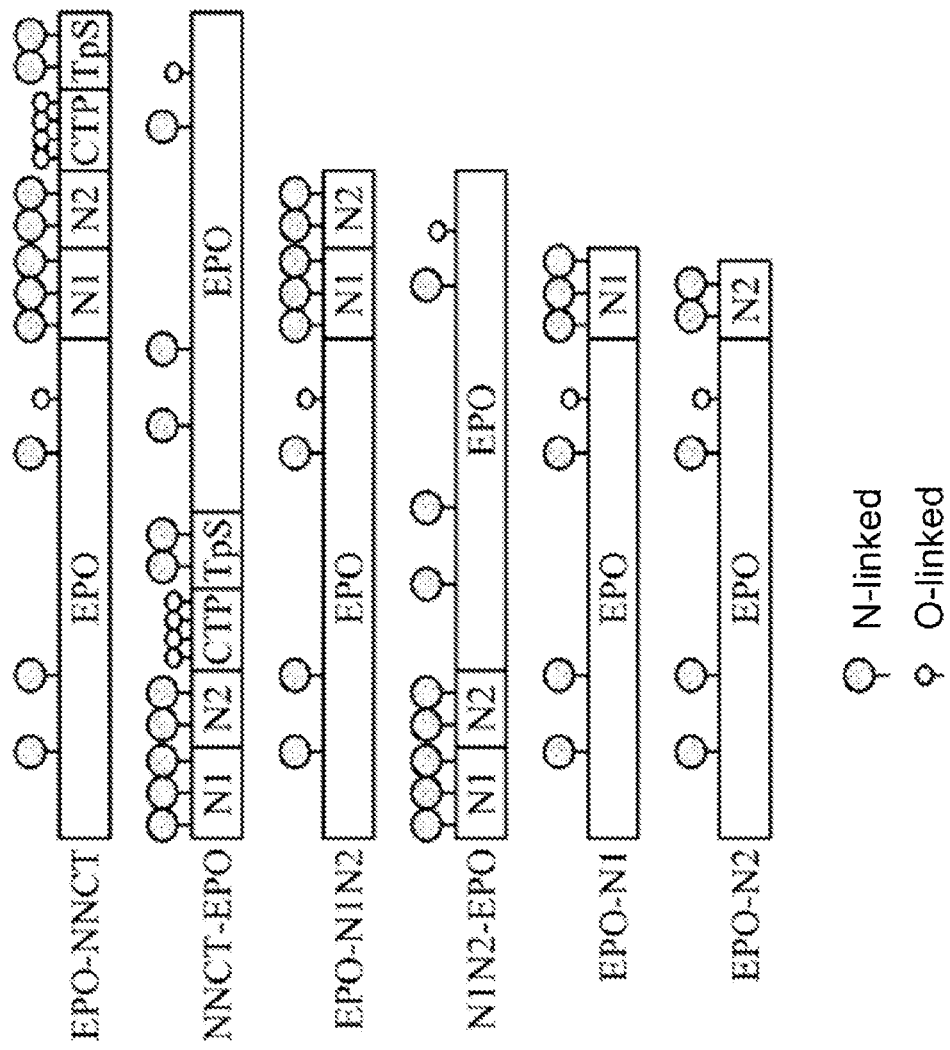
FIG. 1 illustrates the plasmid construction of EPO-NNCT (SEQ ID NO: 5), NNCT-EPO (SEQ ID NO: 6), EPO-N1N2 (SEQ ID NO: 7), N1N2-EPO (SEQ ID NO: 8), EPO-N1 (SEQ ID NO: 9), and EPO-N2 (SEQ ID NO: 10) according to the embodiments of the present invention.

The highly glycosylated peptide is fused with an EPO to form the recombinant protein of the present invention. The highly glycosylated peptide can be located on the N-terminal end (N-ter) or carboxy-terminal end (C-ter) of the EPO, and the number of the highly glycosylated peptide is not limited. For example, one or more the same or different highly glycosylated peptide (s) can be attached to N-terminal end and/or C-terminal end of the EPO. The recombinant protein containing the highly glycosylated peptide has a longer half-life and higher activity. In one embodiment, the highly glycosylated peptide (SEQ ID NO: 1 and/or 2) can be located on the N-ter or C-ter of EPO, as shown in FIG. 1.

The highly glycosylated peptide includes, but is not limited to, SEQ ID NO: 1 and/or 2. One or more the same or different highly glycosylated peptide(s) can be attached to the C-ter of EPO. For example, SEQ ID NO: 1 or 2 is attached to the C-ter of EPO; or two or more SEQ ID NO: 1 or 2 are attached to the C-ter of EPO; or SEQ ID NO: 1 and 2 are attached to the C-ter of EPO, sequentially; or SEQ ID NO: 2 and 1 are attached to the C-ter of EPO, sequentially. In another embodiment, SEQ ID NO: 1 and 2 are attached to the C-ter of EPO, sequentially.

The recombinant protein of the present invention further comprises a carboxy terminal peptide of human chorionic gonadotropin (hCG).

As used herein, the phrase "carboxy terminal peptide of hCG" (hereinafter referred to as CTP) refers to an amino acid sequence found at the carboxy terminus of human chorionic gonadotropin beta subunit which extends from amino acid 112-118 to residue 145 at the C-terminus or to a portion, or a variant or analog thereof, which has equivalent biological activity. The CTP sequence peptide is 28, 29, 30, 31, 32, 33 or 34 amino acids long and commences at position 112, 113, 114, 115, 116, 117, or 118 of the hCG amino acid sequence.

The CTP of the present invention includes, but is not limited to, SEQ ID NO: 3, or a sequence having at least 65%, 70%, 80%, 90% sequence identity to SEQ ID NO: 3, preferably at least 95% sequence identity.

The CTP of the invention may be attached to EPO (at the N-ter or C-ter) and/or the highly glycosylated peptide (at the N-ter or C-ter). The amount of the CTP is not limited. For example, one or more the same or different CTP of hCG can be attached to the N-ter of the EPO or C-ter of the highly glycosylated peptide(s) of the invention.

The CTP of the present invention may acts as a protectant against degradation of proteins or peptides. In the present application, the CTP of hCG can extends circulatory half-life of recombinant proteins, and enhances the potency of recombinant proteins.

The invention further comprises a carboxy terminal peptide of thrombopoietin (TPO).

As used herein, the phrase "carboxy terminal peptide of thrombopoietin" (hereinafter referred to as TpS) refers to amino acids at positions 176 to 353 of thrombopoietin, particularly the amino acids at positions 337 to 353 of thrombopoietin, or a variant or analog thereof, which has equivalent biological activity.

The TpS of the invention includes, but is not limited to, SEQ ID NO:4, or a sequence having at least 65%, 70%, 80%, or 90% sequence identity to SEQ ID NO: 4, preferably at least 95%, or 99% sequence identity.

The TpS of the present invention may be attached to the EPO (at the N-ter or C-ter), the highly glycosylated peptide (at the N-ter or C-ter) and/or the CTP (at the N-ter or C-ter), and the amount of the TpS is not limited. In one embodiment, one or more the same or different TpS can be attached to the N-ter of the EPO or C-ter of the highly glycosylated peptide. In another embodiment, one or more the same or different TpS can be attached to the N-ter of EPO or the C-ter of the CTP.

The TpS of the present application may acts as a protectant against degradation of proteins or peptides derived therefrom. The TpS can extend circulatory half-life of the recombinant proteins, and enhance the potency of the recombinant proteins.

In the present invention, the amount and arrangement of EPO, the highly glycosylated peptide, CTP, and TpS are not limited.

In one embodiment, the recombinant protein of the present invention comprises SEQ ID NOS: 1, 2, 3, and 4.

In another embodiment, the recombinant protein of the present invention may be selected from SEQ ID NO: 5 (EPO-NNCT), 6 (NNCT-EPO), 7 (EPO-N1N2), 8 (N1N2-EPO), 9 (EPO-N1), or 10 (EPO-N2).

The highly glycosylated peptide, CTP, and TpS also can be modified by deletion, substitution, insertion and/or chemical modification. The method and process of the amino acid deletion, substitution, insertion and/or chemical modification are well known in the art, and the highly glycosylated peptide, CTP, and TpS still maintain the original activity after modification.

In one embodiment, modifications include, but are not limited to, N terminus modification, C terminus modification, polypeptide bond modification, such as $CH_2$—NH, $CH_2$—S, $CH_2$—S=O, O=C—NH, $CH_2$—O, $CH_2$—$CH_2$, S=C—NH, CH=CH, or CF=CH, backbone modifications, and residue modification. Methods for preparing peptidomimetic compounds are well known in the art and can be referred to Quantitative Drug Design, C. A. Ramsden Gd., Chapter 17.2, F. Choplin Pergamon Press (1992).

In one embodiment, the peptide bond (—CO—NH—) of the polypeptide can be substituted by, such as, N-methyl bond (—N($CH_3$)—CO), ester bond (—C(R)H—COOC(R)—N—), ketomethylen (—CO—$CH_2$), α-aza bond (—NH—N(R)—CO—), where R is any alkyl, hydroxyethylene bond (—CH(OH)—$CH_2$—), thioamide (—CS—NH—), alkene bonds (—CH=CH—), amide bond (—NH—CO—), or polypeptide derivative (—N(R)—$CH_2$—CO—).

The present invention further provides a polynucleotide encoding the recombinant protein of the present invention.

The phrase "a polynucleotide or nucleotide" refers to a single or double stranded nucleic acid sequence which be isolated and provided in the form of an RNA sequence, a complementary polynucleotide sequence (cDNA), a genomic polynucleotide sequence and/or a combination of the above.

The polynucleotides of the present invention may be prepared using PCR techniques, or any other method or procedure known to one skilled in the art. The procedure involves the ligation of two different DNA sequences (See, for example, "Current Protocols in Molecular Biology", eds. Ausubel et al., John Wiley & Sons, 1992).

The polynucleotides of the invention may be inserted into expression vectors to enable expression of the recombinant protein. In one embodiment, the expression vector includes additional sequences which render this vector suitable for replication and integration in prokaryotes or eukaryotes. In another embodiment, expression vectors comprise transcription and translation initiation sequences (e.g., promoters or enhances) and transcription and translation terminators (e.g., polyadenylation signals).

A variety of prokaryotic or eukaryotic cells can be used as host-expression systems to express the polypeptides of the present invention. In one embodiment, these expression systems include, but are not limited to, microorganisms, such as bacteria, yeast, plant cell, eukaryotes (e.g. mammalian cells, CHO cells), etc.

Methods for transformation can be found in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986], and include, for example, stable or transient transfection, lipofection, electroporation and infection with recombinant viral vectors.

The present invention of the invention further provides a composition, comprising the recombinant protein of the invention and a physiologically acceptable carrier or excipient.

The phrases "pharmaceutically acceptable carrier or excipient" which be interchangeably used refer to a carrier, excipient or adjuvant that does not cause significant irritation to an organism and does not abrogate the biological activity and properties of the administered compound. The carrier comprises, but is not limited to polyethylene glycol (PEG), a biocompatible polymer with solubility in both organic and aqueous media. The excipients include, but are not limited to calcium carbonate, calcium phosphate, various sugars and starch, cellulose derivatives, gelatin, vegetable oils and polyethylene glycols.

The composition of the present invention can be used to treat a patient having anemia, an anemic patient having chronic renal insufficiency, an anemic patient having end stage renal disease, an anemic patient undergoing dialysis, an anemic patient having chronic renal failure, an anemic HIV infected patient, an anemic patient having cancer, an anemic patient undergoing chemotherapy, and an anemic patient scheduled to undergo non-cardiac, non-vascular surgery.

After an effective amount of the composition of the present invention is administrated to an anemia patient, the hematocrit (Ht) of anemia patient can be increased significantly, and the recombinant EPO with high glycosylation of the present invention has a longer half-life in a subject. The recombinant EPO with high glycosylation of the present invention has a longer half-life than that of the commercial EPO products (e.g., Eprex® and Aranesp®). Eprex® is the brand name for epoetin alfa (rch), which is recombinant human erythropoietin (EPO) expressed in Chinese hamster ovary cells (rch) and has a 165 amino acid sequence identical to that of human urinary EPO. Aranesp® is the brand name for darbepoetin alfa, which is recombinant human erythropoietin (EPO) expressed in Chinese hamster ovary cells and has a 165-amino acid protein that differs from recombinant human erythropoietin in containing 5 N-linked oligosaccharide chains, whereas recombinant human erythropoietin contains 3 chains. For example, the high-glycosylated EPO of the present invention has a half-life at least about 1 time longer than the commercial EPO products, preferably, 2 times, more preferably, 3 times. In another embodiment, the high-glycosylated EPO of the present invention has a longer half-life, a higher AUC (area under curve) and Cmax, and a longer Tmax values than that of the commercial EPO products (e.g., Eprex® and Aranesp®).

The phrase "therapeutically effective" generally refers to from about 1 to 10000 I.U./kg, preferably from about 50 to 2000 I.U./kg, more preferably from about 50 to 600 I.U./kg, and most preferably from about 50 to 300 I.U./kg body weight. The formulations of the present invention may be administered at any desired frequency or time interval between administrations. A dosing regimen, the subject is administered the sustained release formulations of the present invention thrice per two weeks, once per week, once per two weeks, once per three weeks, once per month, once per five weeks, once per six weeks, or at more frequent or less frequent intervals, or at any combination of frequencies or time intervals as desired. The dosage required will vary according to a number of factors known to those skilled in the art, including, but not limited to, the compound or compounds used, the species of subject, the size of the subject, and the severity of the associated disease condition that anemia. A preferred dosing regimen may be once per three weeks, particularly for subjects receiving chemotherapy for the treatment of cancer, since many chemotherapeutic regimens are administered on a once per three-week schedule.

EXAMPLES

Example 1

Host Cells

Cells were purchased from the Culture Collection and Research Center (CCRC, 60133) of Food Industry Research and Development Institute, Taiwan. CHO dfhr-cells were cultured in IMDM medium (Isocoves Modified Dulbecco's Medium, IMDM, Gibco Cat. 12200-36) supplemented with 10% fetal bovine serum (Gibco Cat. 10091148) plus hypoxanthine and thymidine (Gibco, Cat. 11067-030) and 2 mM L-glutamine (Gibco Cat. 25030-081). Dhfr(−) marker was used for amplification and selection. Expression of the dhfr gene could be amplified by challenging with the dihydrofolate reductase inhibitor, methorexate (MTX, Sigma Cat no. M8407). When the dfhr genes were amplified, other neighboring genes often were co-amplified, so that after each round of amplification cells were subcloned to select clones with increased production rates. Cells were cultured in a 37 humified 95% air/5% $CO_2$ incubator (Model 3326, Forma scientific).

Example 2

Construction of the Expression Vectors

2.1 EPO-NNCT

EPO-NNCT gene fragment was obtained using assembly PCR method and then inserted into pcDNA3.1/Neo (+)/DHFR vector, yielding pND/EPO-NNCT. The expression vector construct contained the neomycin-resistance gene as a selective marker. EPO-NNCT gene was shown in FIG. 1, wherein the "EPO" is an erythropoietin, "N1" is highly glycosylated peptide 1 (SEQ ID NO: 1), "N2" is highly glycosylated peptide 2 (SEQ ID NO: 2), "CTP" is the carboxy terminal peptide of hCG (SEQ ID NO: 3), and "TpS" is the carboxy terminal peptide of thrombopoietin (SEQ ID NO: 4).

2.2 NNCT-EPO

The DNA fragment of NNCT was reproduced by PCR using LSP—N—S1 primer (3'-cctagggccaccatgggggtgcacgaatgtcctgcctggctgtggcttctcctgtccctgctgtcgctccctctgg-5'; SEQ ID NO: 11), LSP—N—S2 primer (3'-ctgtccctgctgtcgctccctctgggcctccagtcctgggcgaggccgagaatatcacgacgggcggtaac-5'; SEQ ID NO: 12), and ENNCT1-A primer (3'-ctcggctgtcacagatgaggcgtggtggggcccttcctgagacagattctgggagtgggtgtaggatg-5'; SEQ ID NO: 13) from pND/EPO-NNCT plasmid to obtain NNCT-EPO fragment as shown in FIG. 1. The NNCT-EPO fragment then was inserted into an expression vector to obtain pPD/NNCT-EPO vector. The expression vector contained the puromycin-resistance gene as a selective marker.

2.3 EPO-N1N2

The DNA fragment of EPO-N1N2 was reproduced by PCR using E-S primer (3'-cctagggccaccatgggggtgcacgaatgtcctgcc-5'; SEQ ID NO: 14) and ENNCT2-A primer (3'-gtataccctacagctgcagagtctcgttcacctgggaagag-5'; SEQ ID NO: 15) from pND/EPO-NNCT plasmid to obtain EPO-N1N2 fragment as shown in FIG. 1. The EPO-N1N2 fragment then was inserted into an expression vector to obtain pPD/EPO-N1N2 vector. The expression vector contained the puromycin-resistance gene as a selective marker.

2.4 N1N2-EPO

The DNA fragment of N1N2-EPO was synthesized by GENEWIZ, Inc (as shown in FIG. 1), and it was inserted into an expression vector to obtain pPD/N1N2-EPO vector. The expression vector contained the puromycin-resistance gene as a selective marker.

2.5 EPO-N1

The DNA fragment of EPO-N1 was reproduced by PCR using E-S primer (3'-cctagggccaccatgggggtgcacgaatgtcctgcc-5'; SEQ ID NO: 14) and ENNCT4-A primer (3'-gtatacctagtctgggacagtgatattctc-5'; SEQ ID NO: 16) from pND/EPO-NNCT plasmid as shown in FIG. 1. The EPO-N1 fragment was inserted into an expression vector to obtain pPD/EPO-N1. The expression vector contained the puromycin-resistance gene as a selective marker.

2.6 EPO-N2

The DNA fragment of EPO-N2 was obtained by PCR method using E-S primer (3'-cctagggccaccatgggggtgcacgaatgtcctgcc-5'; SEQ ID NO: 14) and ENNCT5-A primer (3'-gtataccctaca gctgcagagtctcgttcacctgggaagagttgaccaacagtctgtccctgtcctgcaggcctccc-5'; SEQ ID NO: 17) from pND/EPO-NNCT plasmid to obtain EPO-N2 fragment as shown in FIG. 1. EPO-N2 fragment then was inserted into an expression vector to obtain pPD/N1 plasmid. The expression vector contained the puromycin-resistance gene as a selective marker.

Example 3

Establishment of the Recombinant Cell Lines

Vector containing EPO-NNCT gene was transfected into CHO dhfr-cells by electroporation (PA4000 PulseAgile® electroporator, Cyto Pulse Sciences). Cells were first trypsinized and resuspended at a concentration of $3 \times 10^6$ cells/ml in CP-T buffer (Cyto Pulse Cat. CP-T). 200 µl of cell suspension ($6 \times 10^5$ cells) was mixed with 10 µg pND/BMP2 and electrophoresed. Electrophoresed cells were cultured in a complete medium (IMDM with 10% fetal bovine serum and HT supplement) without selective substance for recovery growth. After 48 hours growth in medium without selective substance, the cells were transferred to the complete medium containing IMDM, 10% fetal bovine serum, L-glutamine and 5 nM MTX, with selective substance. After approximately 2-week culture period, cell lines were transferred to 96-well plates, and cell lines which express high level of rhBMP-2 were selected through quantifying protein level by ELISA. The selected cells were cultured in a selective medium. The cells were diluted to the concentration of 1 cell/100 W and then transferred to a 96-well plate to culture to grow to cell clusters. Cells with high expression level were screened according to the results of ELISA and MTX concentrations were gradually increased from 0.005, 0.01, 0.02 to 0.05 µM.

Example 4

Batch Culture $4 \times 10^5$ cell/ml of recombinant cell line obtained from Example 3 were batch-cultured in 50 ml flask containing serum free medium. Cells were monitored everyday and culture medium was collected to measure the concentration of the EPO and select a high-yield clone under 0.02 µM MTX challenge. In spinner culture, the accumulated productivity of EPO-NNCT was 140.69 µg/ml as shown in Table 1.

TABLE 1

| Results of batch culture | |
|---|---|
| Max. Yield (µg/ml) | 140.9 |
| Max. cell concentration ($10^6$ cell/ml) | 2.42 |
| IVC ($10^6$ cell-day) | 14.60 |
| q (pg/cell/day) | 9.63 |

Example 5

Bioactivity Assay

Figure 2:
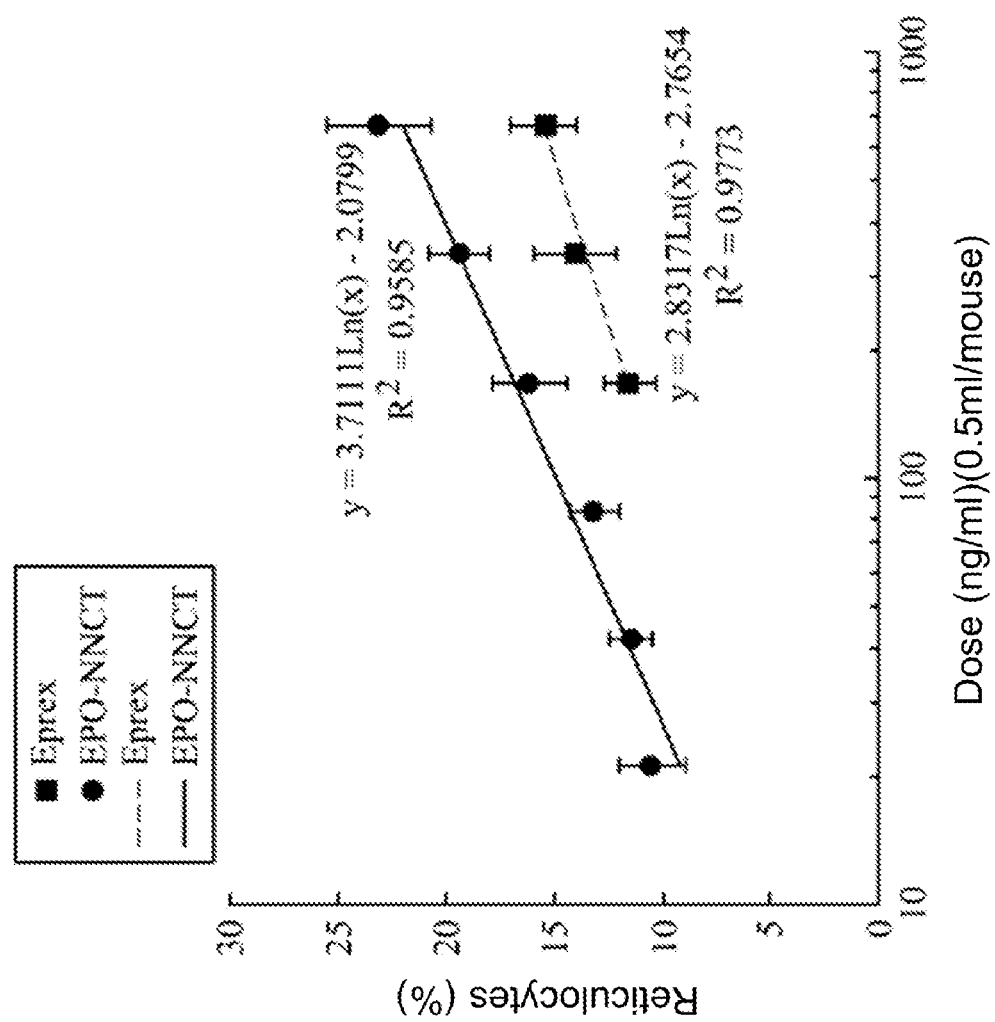
FIG. 2 illustrates the comparison of activity levels between EPO-NNCT (SEQ ID NO: 5) of the present invention and commercial Eprex®.

The process and procedure of the example were carried out according to the disclosure of European Pharmacopeia 5.2 (Erythropoietini solution concentrata). Female 8-week-old BALB/c mice were classified into two groups, and injected subcutaneously with 21, 42, 84, 168, 336, and 672 ng/ml of EPO-NNCT (SEQ ID NO: 5) of the invention and Eprex®, individually. After injection, the 0.25 ml whole blood was collected. After the cells were stained, the cells were analyzed by flow cytometry and CellQuest Pro software, and the results were shown in Table 2. Referring to FIG. 2, in the same dosage, the average number of reticulocytes of the mice administered with EPO-NNCT (SEQ ID NO: 5) of the present invention was higher than that of the mice administered with Eprex®.

TABLE 2

Amount of Reticulocytes after injection

| | Subcutaneous injection (ng/ml) | Reticulocytes (mean %) |
|---|---|---|
| EPO-NNCT (SEQ ID NO: 5) | 672 | 23.15 |
| | 336 | 19.45 |
| | 168 | 16.14 |
| | 84 | 13.17 |
| | 42 | 11.47 |
| | 21 | 10.52 |
| Eprex ® | 672 | 15.50 |
| | 336 | 14.05 |
| | 168 | 11.57 |

25 female 8-week-old BALB/c mice were classified into five groups, and injected subcutaneously with 336 ng/ml of EPO-NNCT (SEQ ID NO: 5) and Eprex®, individually. The mice whole blood was collected at 4 to 9, and 13 days after injection. The percentage of reticulocyte was determined by flow cytometry and analyzed by CellQuest Pro software. As shown in Table 3, the amount (mean %) of reticulocytes was highest at Day 7 in the mice injected with the EPO-NNCT (SEQ ID NO: 5) of the invention and significantly higher than that of Eprex®.

TABLE 3

Amount of Reticulocytes at different day after injection

| | Day | Reticulocytes (Mean %) | S.D. | CV |
|---|---|---|---|---|
| EPO-NNCT (SEQ ID NO: 5) | 5 | 20.33 | 2.38 | 11.70 |
| | 6 | 27.26 | 1.99 | 7.29 |
| | 7 | 28.12 | 2.11 | 7.51 |
| | 8 | 25.42 | 2.17 | 8.55 |
| | 9 | 16.37 | 3.09 | 18.89 |
| | 13 | 5.21 | 0.53 | 10.19 |
| Eprex ® | 5 | 11.28 | 1.56 | 13.86 |
| | 6 | 7.42 | 0.81 | 10.97 |
| | 7 | 6.35 | 1.16 | 18.22 |
| | 8 | 11.11 | 1.22 | 10.95 |
| | 9 | 10.76 | 2.40 | 22.31 |
| | 13 | 8.61 | 0.92 | 10.67 |

Example 6

Figure 3:
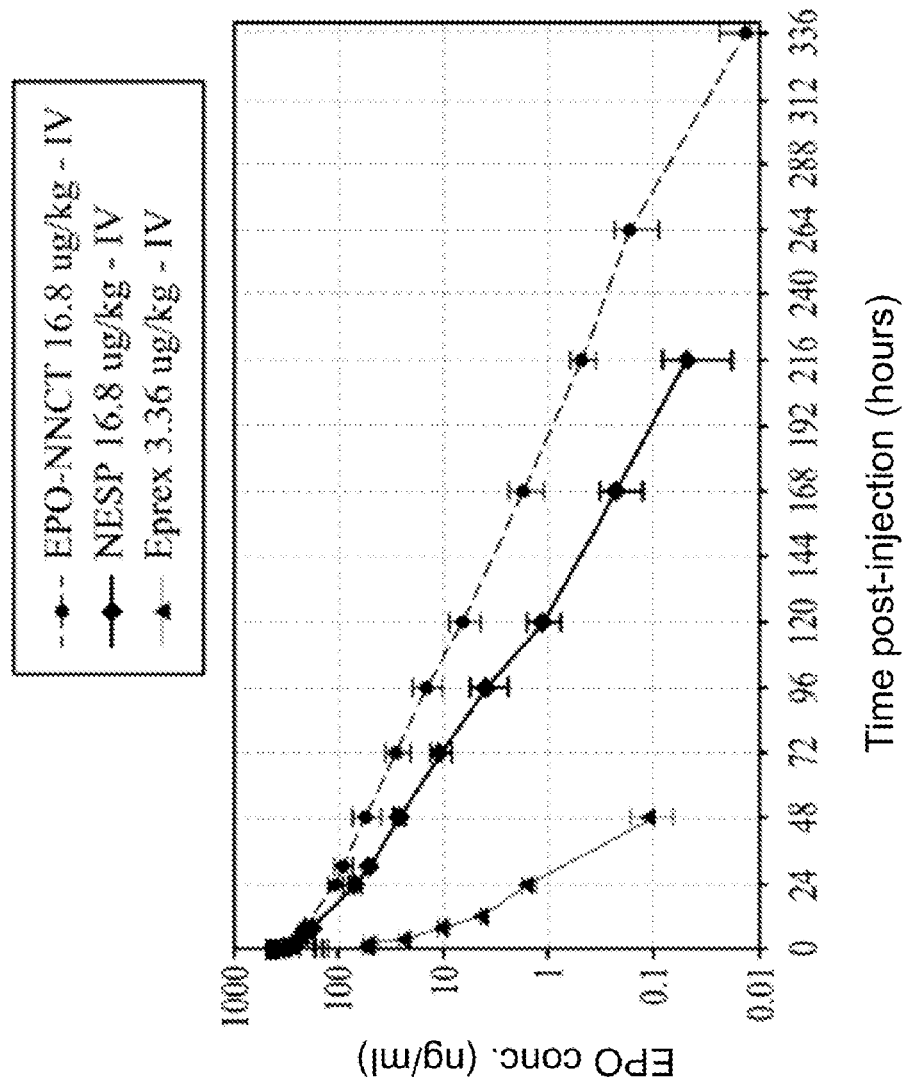
FIG. 3 illustrates the comparison of pharmacokinetic properties (PK) between EPO-NNCT (SEQ ID NO: 5) of the present invention and commercial Eprex® (intravenous injection).
Figure 4:
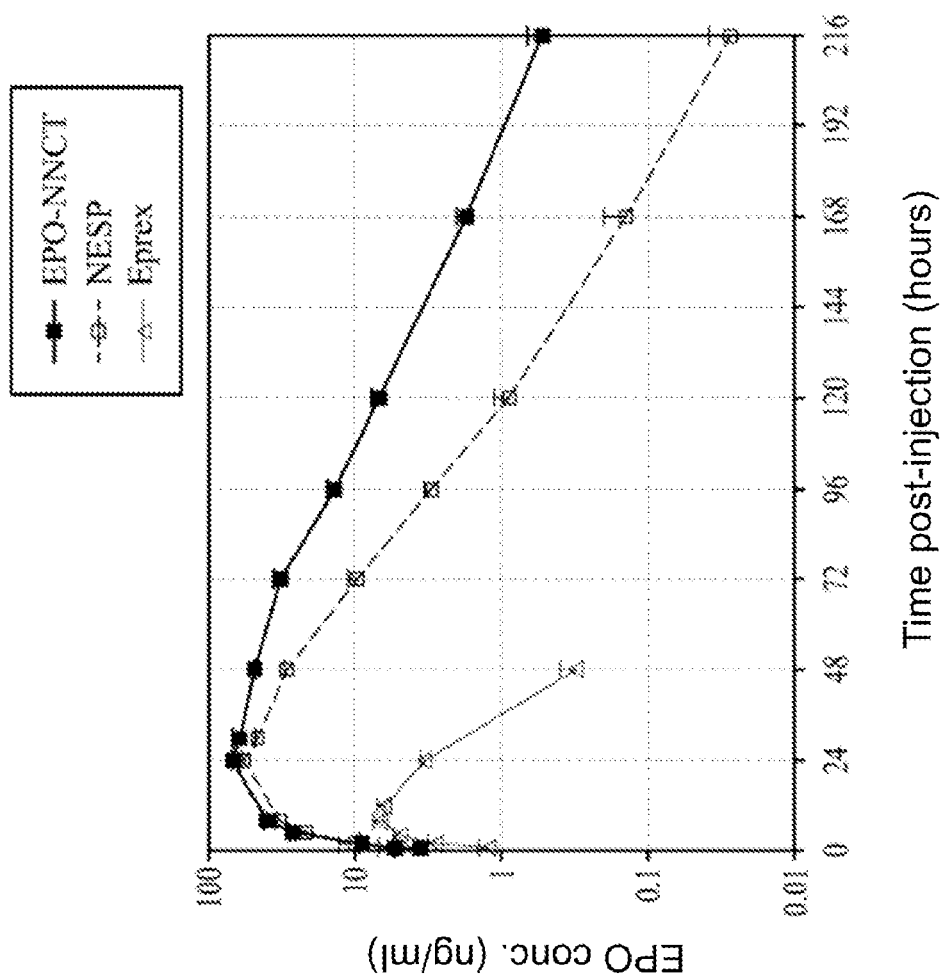
FIG. 4 illustrates the comparison of pharmacokinetic properties (PK) between EPO-NNCT (SEQ ID NO: 5) of the present invention and commercial Eprex® (subcutaneous injection).
Figure 5:
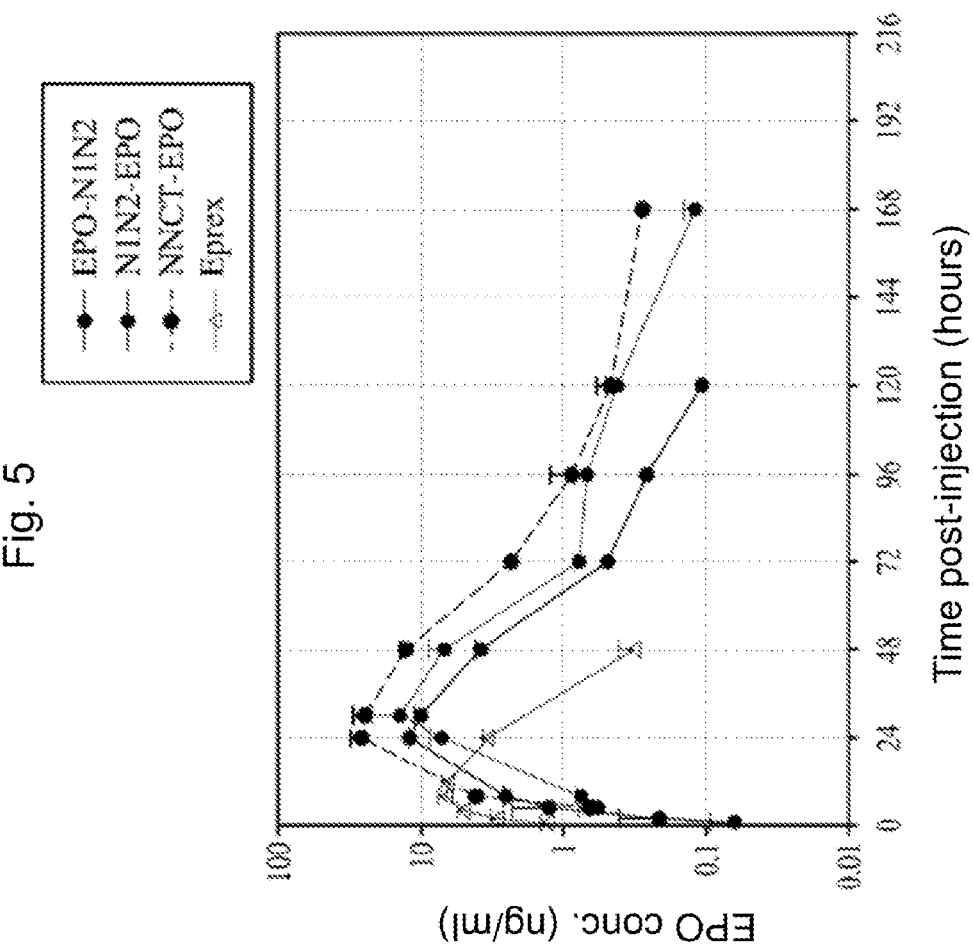
FIG. 5 illustrates the comparison of pharmacokinetic properties (PK) between EPO-N1N2 (SEQ ID NO: 7), N1N2-EPO (SEQ ID NO: 8), NNCT-EPO (SEQ ID NO: 6) of the present invention and commercial Eprex® (subcutaneous injection).

Pharmacokinetic Assay 14 female 8-week-old BALB/c mice were classified into four groups, and intravenously and subcutaneously injected with 2000 IU/kg of EPO-NNCT (SEQ ID NO: 5) of the invention, Eprex®, and Aranesp®, individually. The mice blood was collected at 5 min, 10 min, 30 min, 1 hr, 2 hr, 5 hr, 8 hr, 24 hr, 30 hr, 48 hr, 72 hr, 96 hr, 120 hr, 168 hr, 216 hr, 264 hr, and 336 hr after injection, centrifuged to obtain the serum, and then the serum was stored at −70° C. The pharmacokinetic assay was carried out using Quantikine® IVD® Epo ELISA kit to measure the optical density at 450 nm and 600 nm and then analyzed by SoftMax® Pro 5 software. The results are shown in Table 4. Referring to FIGS. 3-4, compared to Eprex® and Aranesp®, EPO-NNCT (SEQ ID NO: 5) of the present invention had a longer half-life (about 25-26 hours), and a higher AUC (area under the curve) value (about 8387-4502 ng·hr/ml).

TABLE 4

Pharmacokinetic properties of EPO-NNCT

| | half-life (hr) | AUC (ng · hr/ml) | Cmax (ng/ml) | Tmax (hr) |
|---|---|---|---|---|
| intravenous injection | | | | |
| EPO-NNCT (n = 2) | 25.03 | 8387.44 | — | — |
| Aranesp ® (n = 2) | 17.89 | 5694.75 | — | — |
| Eprex ® (n = 3) | 6.35 | 269.96 | — | — |
| subcutaneous injection | | | | |
| EPO-NNCT (n = 2) | 26.53 | 4502.90 | 68.19 | 24 |
| Aranesp ® (n = 2) | 17.78 | 2547.34 | 58.16 | 24 |
| Eprex ® (n = 3) | 7.14 | 169.55 | 6.88 | 10 |

Similarly, compared to Eprex®, EPO-N1N2 (SEQ ID NO: 7), N1N2-EPO (SEQ ID NO: 8), and NNCT-EPO (SEQ ID NO: 6) of the present invention also had a longer half-life (21-30 hours), and a higher AUC (Area Under Curve) value (370-981 ng·hr/ml), as shown in Table 5.

Further, EPO-N1 (SEQ ID NO: 9) and EPO-N2 (SEQ ID NO: 10) had a Tmax of about 24 hours. Accordingly, it is known that EPO-N1 (SEQ ID NO: 9) and EPO-N2 (SEQ ID NO: 10) had a higher Tmax as compared to commercial Eprex®.

TABLE 5

Pharmacokinetic properties of EPO-N1N2, N1N2-EPO, NNCT-EPO and Eprex ® (subcutaneous injection)

| | half-life (hr) | AUC (ng · hr/ml) | Cmax (ng/ml) | Tmax (hr) |
|---|---|---|---|---|
| EPO-N1N2 (SEQ ID NO: 7) | 21.76 | 370.47 | 11.77 | 24 |
| N1N2-EPO (SEQ ID NO: 8) | 30.14 | 448.04 | 13.78 | 30 |
| NNCT-EPO (SEQ ID NO: 6) | 25.50 | 981.63 | 26.18 | 24 |
| Eprex ® | 7.14 | 169.55 | 6.88 | 10 |

Although preferred embodiments are disclosed as above, they cannot be used to limit the preset invention, and anyone skilled in the art can make some changes and modifications without exceeding the spirit and scope of the present invention, and thus the scope of the present invention will be limited only by the appended claims.

SYMBOL DESCRIPTION

EPO: Erythropoietin
N1: Highly glycosylated fragment 1
N2: Highly glycosylated fragment 2
CTP: Carboxy terminal peptide of human chorionic gonadotropin
TpS: Carboxy terminal peptide of thrombopoietin

The invention claimed is:

1. A recombinant protein, comprising an erythropoietin and a highly glycosylated peptide, wherein the highly glycosylated peptide comprises the sequence of SEQ ID NO: 1 and/or 2.

2. The recombinant protein according to claim 1, wherein the carboxy-terminal end of the erythropoietin is attached to the highly glycosylated peptide.

3. The recombinant protein according to claim 1, wherein the amino-terminal end of the erythropoietin is attached to the highly glycosylated peptide.

4. The recombinant protein according to claim 1, further comprising a carboxy terminal peptide of human chorionic gonadotropin.

5. The recombinant protein according to claim 4, wherein the carboxy terminal peptide of human chorionic gonadotropin comprises the sequence of SEQ ID NO: 3.

6. The recombinant protein according to claim 5, wherein the carboxy-terminal end of the highly glycosylated peptide is attached to the carboxy terminal peptide of human chorionic gonadotropin.

7. The recombinant protein according to claim 4, further comprising a carboxy terminal peptide of thrombopoietin.

8. The recombinant protein according to claim 7, wherein the carboxy terminal peptide of thrombopoietin comprises the sequence of SEQ ID NO: 4.

9. The recombinant protein according to claim 7, wherein the carboxy-terminal end of the carboxy terminal peptide of human chorionic gonadotropin is attached to the carboxy terminal peptide of thrombopoietin.

10. The recombinant protein according to claim 1, further comprising a carboxy terminal peptide of thrombopoietin.

11. The recombinant protein according to claim 10, wherein the carboxy terminal peptide of thrombopoietin comprises the sequence of SEQ ID NO: 4.

12. The recombinant protein according to claim 10, wherein the carboxy-terminal end of the carboxy terminal peptide of human chorionic gonadotropin is attached to the carboxy terminal peptide of thrombopoietin.

13. The recombinant protein according to claim 1, wherein the recombinant protein comprises the sequence of SEQ ID NO: 5.

14. The composition comprises the recombinant protein of claim 1 and a pharmaceutically acceptable carrier or adjuvant.

* * * * *